United States Patent
Schwab et al.

(10) Patent No.: US 9,434,619 B2
(45) Date of Patent: Sep. 6, 2016

(54) GRAPHENE NANORIBBON PRECURSORS AND MONOMERS SUITABLE FOR PREPARATION THEREOF

(71) Applicants: BASF SE, Ludwigshafen (DE); Max-Planck-Gesellschaft zur Foerderung der Wissenschaften e.V., Munich (DE)

(72) Inventors: Matthias Georg Schwab, Mannheim (DE); Klaus Muellen, Cologne (DE); Xinliang Feng, Mainz (DE); Lukas Doessel, Darmstadt (DE)

(73) Assignees: BASF SE, Ludwigshafen (DE); Max-Planck-Gesellschaft zur Foerderung der Wissenshaften e.V., Munich (DE)

( * ) Notice: Subject to any disclaimer, the term of this patent is extended or adjusted under 35 U.S.C. 154(b) by 122 days.

(21) Appl. No.: 14/354,430

(22) PCT Filed: Oct. 24, 2012

(86) PCT No.: PCT/IB2012/055845
§ 371 (c)(1),
(2) Date: Apr. 25, 2014

(87) PCT Pub. No.: WO2013/061258
PCT Pub. Date: May 2, 2013

(65) Prior Publication Data
US 2014/0301936 A1    Oct. 9, 2014

Related U.S. Application Data

(60) Provisional application No. 61/551,466, filed on Oct. 26, 2011.

(51) Int. Cl.
| | |
|---|---|
| C01B 31/02 | (2006.01) |
| C01B 31/04 | (2006.01) |
| B82Y 40/00 | (2011.01) |
| C07C 17/30 | (2006.01) |
| C07C 25/18 | (2006.01) |
| C08G 61/10 | (2006.01) |
| B82Y 30/00 | (2011.01) |

(52) U.S. Cl.
CPC ............ *C01B 31/0446* (2013.01); *B82Y 30/00* (2013.01); *B82Y 40/00* (2013.01); *C07C 17/30* (2013.01); *C07C 25/18* (2013.01); *C08G 61/10* (2013.01); *C01B 2204/06* (2013.01); *C01B 2204/065* (2013.01); *C08G 2261/148* (2013.01); *C08G 2261/312* (2013.01); *C08G 2261/412* (2013.01)

(58) Field of Classification Search
CPC .. C08G 64/30; C08G 64/0208; C01B 31/02; C01B 31/04
See application file for complete search history.

(56) References Cited

U.S. PATENT DOCUMENTS 7,132,294 B2    11/2006    Houser et al.

OTHER PUBLICATIONS

Raza, Hassan, and Edwin C. Kan. "Armchair graphene nanoribbons: Electronic structure and electric-field modulation." Physical Review B 77.24 (2008): 245434.*
El Gemayel, Mirella, et al. "Graphene nanoribbon blends with P3HT for organic electronics." Nanoscale 6.12 (2014): 6301-6314.*
U.S. Appl. No. 14/758,349, filed Jun. 29, 2015, Wonneberger, et al.
Jishan Wu, et al., "Oligomers of Hexa -peri-hexabenzocoronenes as Super-oligophenylenes": Synthesis, Electronic Properties, and Self-assembly, J. Org. Chem., vol. 69, No. 24, Nov. 2, 2004, pp. 8194-8204.
Yang, X., et al., "Two-Dimensional Graphene Nanoribbons", J. Am. Chem. Soc., vol. 130, pp. 4216-4217, (2008).
Stankovich, S., et al., "Synthesis of graphene-based nanosheets via chemical reduction of exfoliated graphite oxide", Carbon, vol. 45, pp. 1558-1565, (2007).

Han, M., et al., "Energy Band-Gap Engineering of Graphene Nanoribbons", Physical Review Letters, vol. 98, pp. 206805-1 to 206805-4, (May 18, 2007).
Chen, Z., et al., "Graphene nano-ribbon electronics", Physica E, vol. 40, pp. 228-232, (2007).
Jiao, L., et al., "Facile synthesis of high-quality graphene nanoribbons", Nature Nanotechnology, vol. 5, pp. 321-325, (May 2010).
Kosynkin, D., et al., "Longitudinal unzipping of carbon nanotubes to form graphene nanoribbons", Nature, vol. 458, pp. 872-876, (Apr. 16, 2009).
Li, X., et al., "Chemically Derived, Ultrasmooth Graphene nanoriboon Semiconductors", Science, vol. 319, (Feb. 29, 2008).
International Search Report Issued Feb. 28, 2013 in PCT/IB/12/055845 Filed Oct. 24, 2012.

* cited by examiner

*Primary Examiner* — Richard M Rump
(74) *Attorney, Agent, or Firm* — Oblon, McClelland, Maier & Neustadt, L.L.P.

(57) ABSTRACT

Provided are graphene nanoribbon precursors comprising repeated units of the general formula (I) in which $R^1$, $R^2$ are each H, halogen, —OH, —NH$_2$, —CN, —NO$_2$ or a hydrocarbyl radical which has 1 to 40 carbon atoms and may be linear or branched, saturated or unsaturated and mono- or poly-substituted by halogen (F, Cl, Br, I), —OH, —NH$_2$, —CN, and/or —NO$_2$, where one or more CH$_2$ groups may also be replaced by —O—, —S—, —C(O)O—, —O—C(O)—, —C(O)—, —NH— or —NR—, in which R is an optionally substituted $C_1C_{40}$-hydrocarbyl radical, or an optionally substituted aryl, alkylaryl or alkoxyaryl radical.

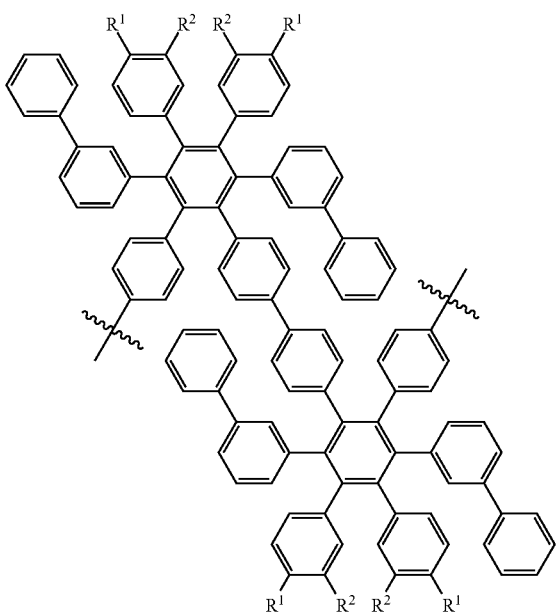

4 Claims, 5 Drawing Sheets

GRAPHENE NANORIBBON PRECURSORS AND MONOMERS SUITABLE FOR PREPARATION THEREOF

Figure 1:
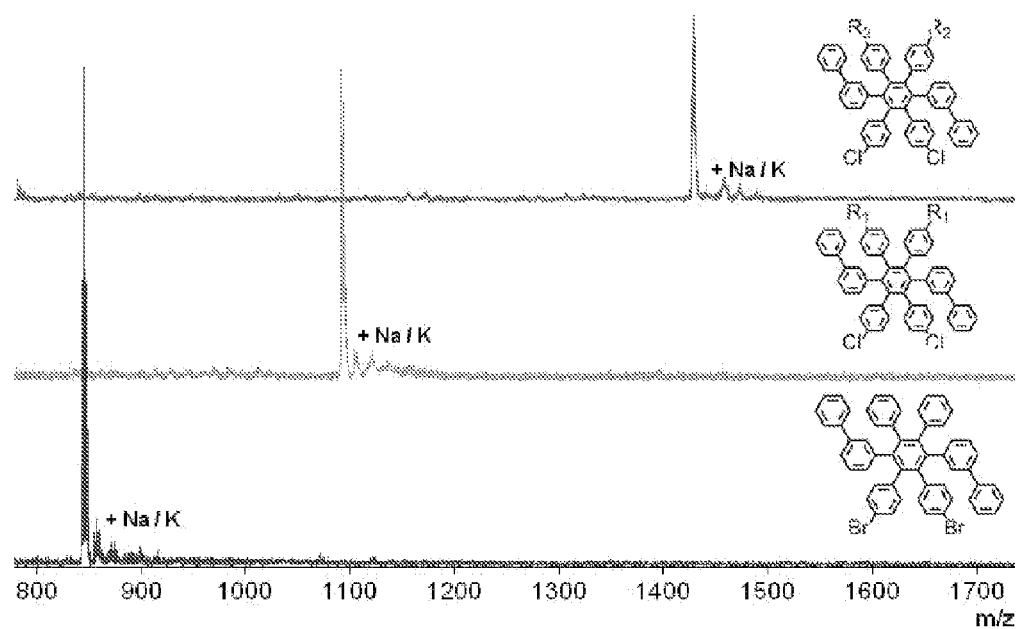

The invention relates to graphene nanoribbon precursors, to graphene nanoribbons obtainable therefrom by oxidative cyclodehydrogenation (intramolecular Scholl reaction), to processes for preparing the graphene nanoribbon precursors, to monomers suitable for preparation of the graphene nanoribbon precursors, and to a process for preparing the monomers.

Graphene nanoribbons (GNRs) are a defined section from the structure of graphene. They consist of monolayer ribbons of $sp^2$-hybridized carbon atoms arranged in a honeycomb and have a high side ratio of length:width, such that they are a quasi-one-dimensional carbon polymorph. Due to the low width of the ribbons in relation to their length, the influence of the edge structure on the electronic properties of the graphene cannot be neglected in graphene nanoribbons. Through the edge structure, it is possible to influence the electronic properties of graphene nanoribbons in a controlled manner.

Graphene itself has already been used in organic electronics, for example as a transparent electrode material or as an active material in field-effect transistors. Graphene, however, does not have a natural band gap, which opposes use as a semiconductor in electronics circuits. However, it has been shown by theoretical models that it is possible in graphene nanoribbons, by controlling the width and the edge structure, to obtain a synthetic band gap. In order to obtain such semiconductive graphene nanoribbons, defect-free graphene ribbons of defined structure with an "armchair" edge structure and a width of <10 nm are needed. These have not been available to date.

It is not possible by "top-down" methods, such as the reduction of graphene oxide (S. Stankovich, D. Dikin, R. Piner, K. Kohlhaas, A. Kleinhammes, Y. Jia, Y. Wu, S. Nguyen, R. Ruoff, *Carbon* 2007, 45, 1558), lithography (M. Han, B. Özyilmaz, Y. Zhang, P. Kim, *Phys. Rev. Lett.*, 2007, 98, 206805, Z. Chen, Y. Lin, M. Rooks, P. Avouris, *Physica E,* 2007, 40, 228), the unzipping of carbon nanotubes (a) L. Jiao, X. Wang, G. Diankov, H. Wang, H. Dai, *Nat. Nanotechnol.* 2010, 5, 321; b) D. Kosynkin, A. Higginbotham, A. Sinitskii, J. Lomeda, A. Dimiev, B. Price, J. Tour, *Nature* 2009, 458, 872) or mechanical exfoliation of graphene (X. Li, X. Wang, L. Zhang, S. Lee, H. Dai, *Science* 2008, 219, 1229), to control the size and edge structure of the graphene nanoribbons obtained. An organic "bottom-up" synthesis, in contrast, allows structural control at the atomic level and is thus suitable for producing GNRs with exactly defined structure.

X. Yang, X. Dou, A. Rouhanipour, L. Zhi, H. Räder, K. Müllen, *J. Am. Chem. Soc.* 2008, 130, 4216 disclose the production of a graphene nanoribbon by cyclodehydrogenation of a suitable polymer precursor according to Scheme 1 below.

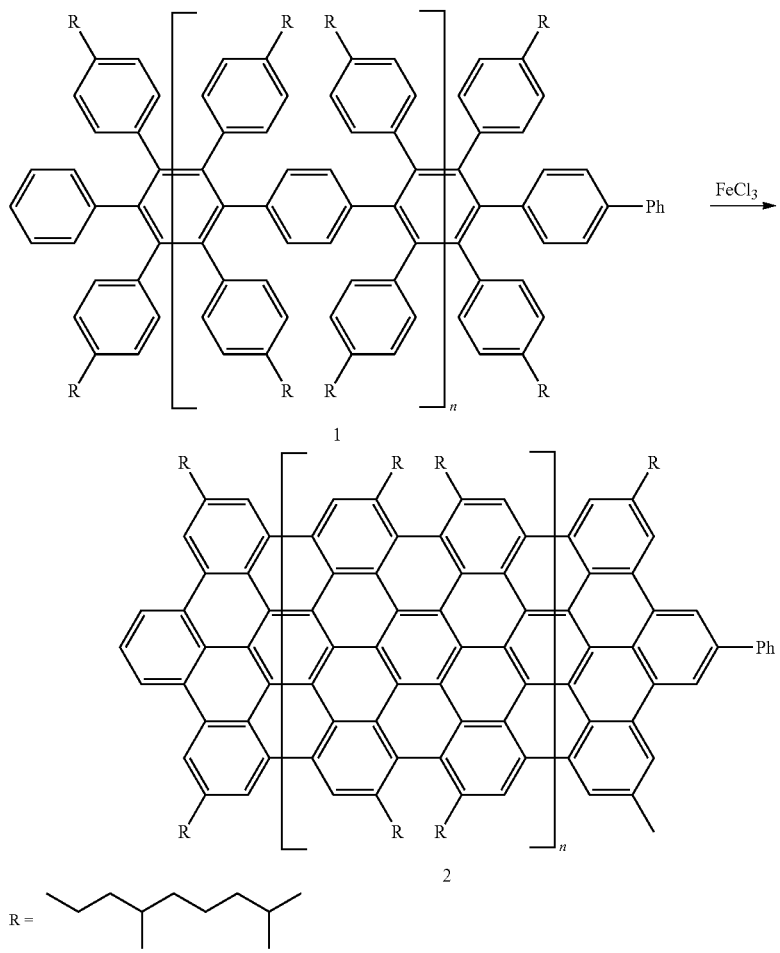

Scheme 1

The synthesis is based on the development of a tailored polymer precursor which is converted to the two-dimensional graphene structure in the last reaction step by oxidative cyclodehydrogenation (intramolecular Scholl reaction). However, full cyclodehydrogenation could not be achieved, and so a study of the electronic properties was not possible due to the presence of defects.

Scheme 2 shows the polymerization to give the polymer precursor.

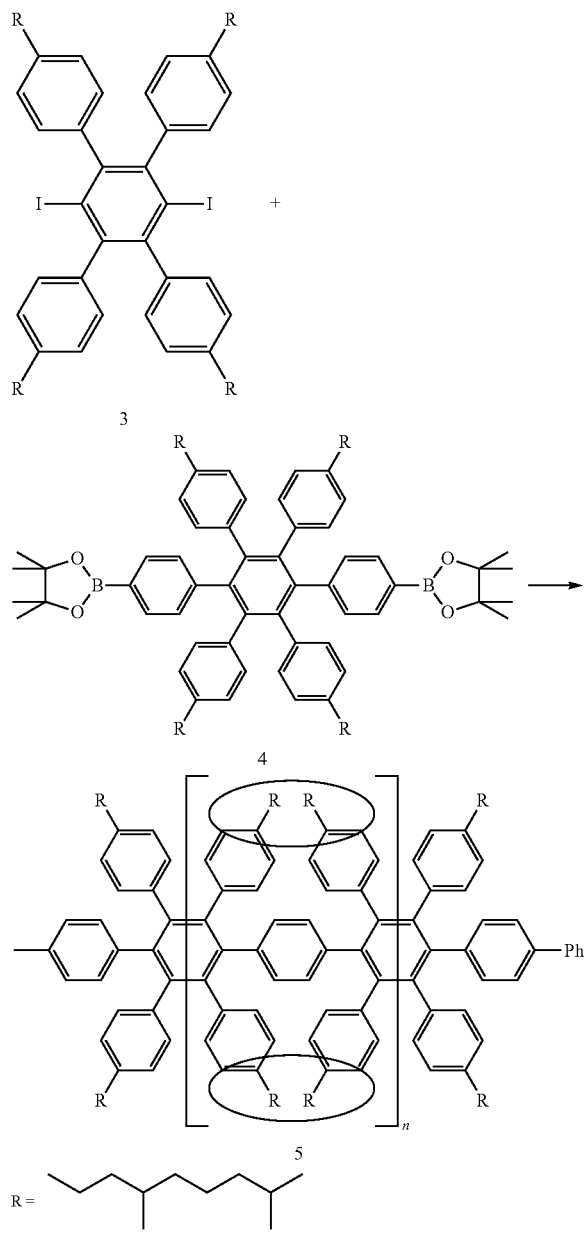

The maximum length of the polymer at about 10 nm is caused by strong steric hindrance during the Suzuki polycondensation from the monomers, since the iodine function in the monomer 3 is screened significantly by two phenyl radicals in the ortho positions, which makes the coupling reaction more difficult. In addition, thermal scission of the carbon-iodine bond is easily possible, and causes chain termination. At the same time, there is spatial hindrance in the polymer as a result of overlapping alkyl radicals, which, in the subsequent cyclodehydrogenation step, hinders formation of aryl-aryl bonds adjacent to these radicals and leads to incomplete cyclodehydrogenation. Another disadvantage is found to be the poly(para-phenylene) structure of the polymer backbone, which allows only a low level of flexibility along the polymer chain. This can result in enhanced aggregation and precipitation of the molecules even during the polymerization, before relatively high molecular weights are attained.

In addition, in the case of polymerization reactions of the $A_2+B_2$ type, the monomers have to be used in exactly stoichiometric amounts, since only low degrees of polymerization are otherwise achieved.

It is an object of the invention to provide a process for producing graphene nanoribbons and suitable graphene nanoribbon precursors, which do not have the disadvantages of the prior art. It is a particular object of the invention to provide graphene nanoribbon precursors which give defect-free graphene nanoribbons with an "armchair" edge structure.

The object was achieved by graphene nanoribbon precursors comprising repeat units of the general formula (I)

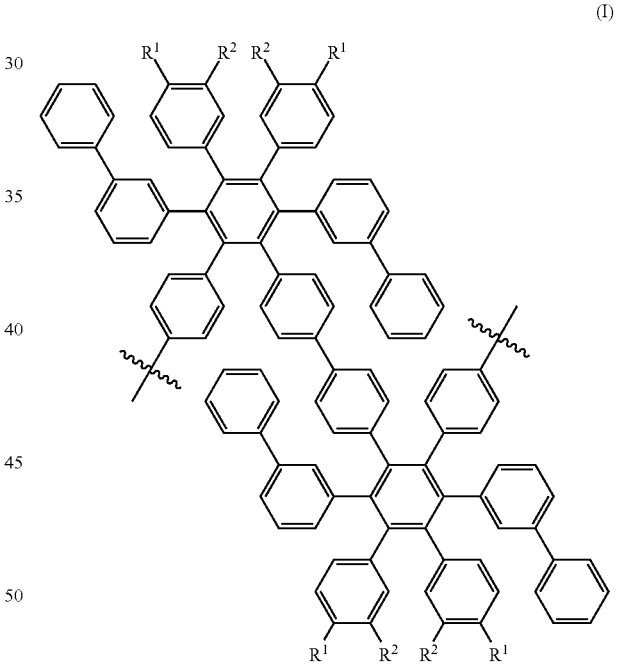

(I)

in which $R^1$, $R^2$ are each H, halogen, —OH, —NH$_2$, —CN, —NO$_2$, a hydrocarbyl radical which has 1 to 40 carbon atoms and may be linear or branched, saturated or unsaturated and mono- or polysubstituted by halogen (F, Cl, Br, I), —OH, —NH$_2$, —CN and/or —NO$_2$, where one or more CH$_2$ groups may also be replaced by —O—, —S—, —C(O)O—, —O—C(O)—, —C(O)—, —NH— or —NR—, in which R is an optionally substituted $C_1$-$C_{40}$-hydrocarbyl radical, or an optionally substituted aryl, alkylaryl or alkoxyaryl radical, and the graphene nanoribbons obtainable therefrom by oxidative cyclodehydrogenation.

The object was also achieved by a process for preparing graphene nanoribbon precursors, comprising the Yamamoto coupling reaction of monomer units of the general formula (II)

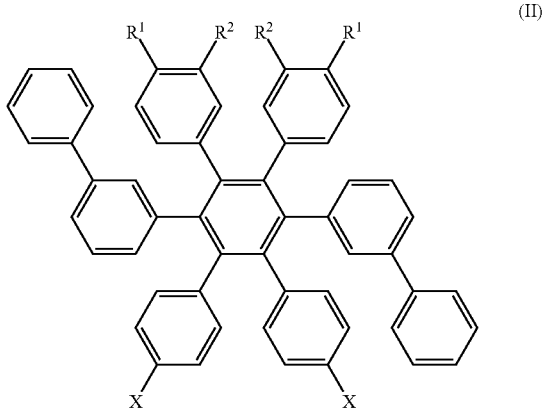

(II)

in which

R$^1$, R$^2$ are each H, halogen, —OH, —NH$_2$, —CN, —NO$_2$ or a hydrocarbyl radical which has 1 to 40 carbon atoms and may be linear or branched, saturated or unsaturated and mono- or polysubstituted by halogen (F, Cl, Br, I), —OH, —NH$_2$, —CN and/or —NO$_2$, where one or more CH$_2$ groups may also be replaced by —O—, —S—, —C(O)O—, —O—C(O)—, —C(O)—, —NH— or —NR—, in which R is an optionally substituted C$_1$-C$_{40}$-hydrocarbyl radical, or an optionally substituted aryl, alkylaryl or alkoxyaryl radical, and X is halogen, trifluoromethylsulfonate or diazonium and by the monomer units of the general formula (II) themselves.

In general, R$^1$, R$^2$ are each H or a saturated or mono- to pentaethylenically and/or -acetylenically unsaturated hydrocarbyl radical which may be mono- to pentasubstituted by the substituents specified.

Preferably, R$^1$, R$^2$ is H or a linear or branched saturated hydrocarbyl radical which may be mono- to pentasubstituted by the substituents specified.

Preferably, R$^1$, R$^2$ are each independently hydrogen, C$_1$-C$_{30}$-alkyl, C$_1$-C$_{30}$-alkoxy, C$_1$-C$_{30}$-alkylthio, C$_2$-C$_{30}$-alkenyl, C$_2$-C$_{30}$-alkynyl, C$_1$-C$_{30}$-haloalkyl, C$_2$-C$_{30}$-haloalkenyl and haloalkynyl, for example C$_1$-C$_{30}$-perfluoroalkyl.

C$_1$-C$_{30}$-Alkyl may be linear or, if possible, branched.

Examples are methyl, ethyl, n-propyl, isopropyl, n-butyl, sec-butyl, isobutyl, tert-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl.

C$_1$-C$_{30}$-Alkoxy groups are straight-chain or branched alkoxy groups, for example methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

The term "alkylthio group" means the same as alkoxy group, except that the oxygen atom in the ether bridge has been replaced by a sulfur atom.

C$_2$-C$_{30}$-Alkenyl groups are straight-chain or branched, for example vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

C$_2$-C$_{30}$-Alkynyl is straight-chain or branched, such as ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

C$_1$-C$_{30}$-Perfluoroalkyl is branched or unbranched, such as —CF$_3$, —CF$_2$CF$_3$, —CF$_2$CF$_2$CF$_3$, —CF(CF$_3$)$_2$, —(CF$_2$)$_3$CF$_3$ or —C(CF$_3$)$_3$.

The terms "haloalkyl, haloalkenyl and haloalkynyl" mean partly or fully halogen-substituted alkyl, alkenyl and alkynyl groups.

Aryl is typically C$_6$-C$_{30}$-aryl and may optionally be substituted, for example phenyl, 4-methylphenyl, 4-methoxyphenyl, naphthyl, biphenylyl, terphenylyl, pyrenyl, fluorenyl, phenanthryl, anthryl, tetracyl, pentacyl and hexacyl.

Preferably, X═Cl or Br. More preferably, R$^1$, R$^2$ are each H or C$_8$-C$_{30}$-alkyl, especially H or C$_{10}$-C$_{26}$-alkyl.

Preferably, R$^2$═H.

Through the Yamamoto coupling reaction proceeding from the inventive monomer units (II), it is possible to produce graphene nanoribbons with generally 3 to 100 and preferably 5 to 50 repeat units (I). The Yamamoto polymerization reaction is additionally not stoichiometry-sensitive like a polymerization reaction of the A$_2$+B$_2$ type.

The angled backbone of the graphene nanoribbon precursor molecule reduces steric hindrance during the polymerization step to form the graphene nanoribbon precursor, and during the subsequent cyclodehydrogenation of the precursor to give the graphene nanoribbon. This allows sterically demanding alkyl radicals to be introduced, which additionally induce increased solubility. The relatively high level of twisting of the angled polymer backbone, which has relatively high flexibility, suppresses the aggregation of the molecules during the polymerization, as a result of which relatively high molecular weights can be achieved.

The synthesis scheme for preparation of monomers of the general formula (II) is shown in Scheme 3.
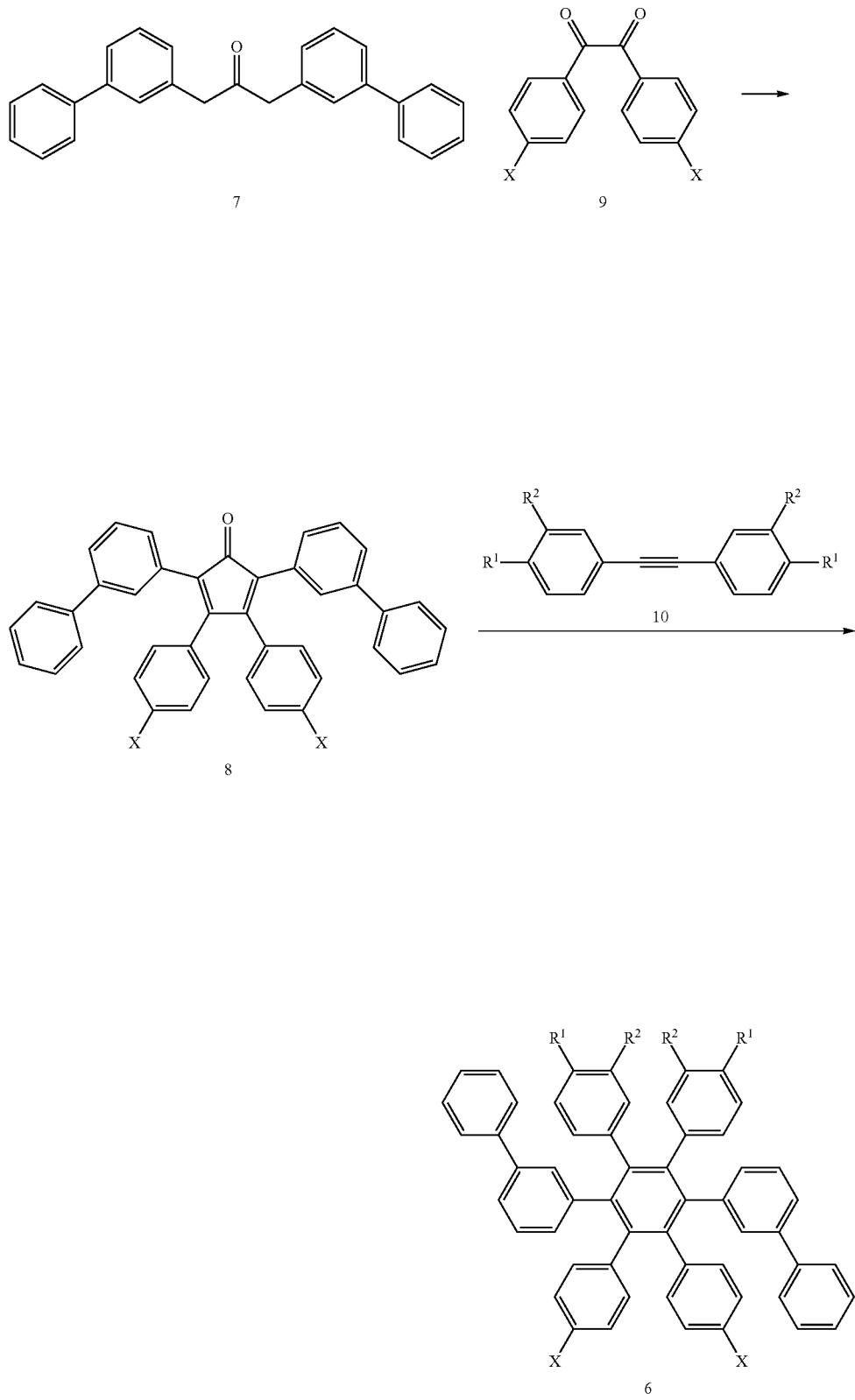
Scheme 3

Proceeding from 1,3-di(biphenyl-3-yl)propan-2-one 7, which already comprises the two flexible meta-biphenyl units, Knoevenagel condensation with 4,4'-dihalobenzil introduces two halogen functions for the later Yamamoto polymerization to obtain the tetraarylcyclopentadienone 8. The cyclopentadienone 8 is converted by Diels-Alder cycloaddition with optionally functionalized tolane 10 to give the monomer 6. This reaction can be performed in a microwave reactor.

The graphene nanoribbon precursors are synthesized from the monomer 6 by Yamamoto polymerization in the presence of a nickel catalyst corresponding to Scheme 4. A suitable catalyst system comprises $Ni(COD)_2$, 1,5-cyclooctadiene and 2,2'-bipyridine in a toluene/DMF mixture as a solvent. The polymers formed can be "end-capped", i.e. the terminal halogen functions can be exchanged for phenyl, by addition of chlorobenzene or bromobenzene.

Scheme 4

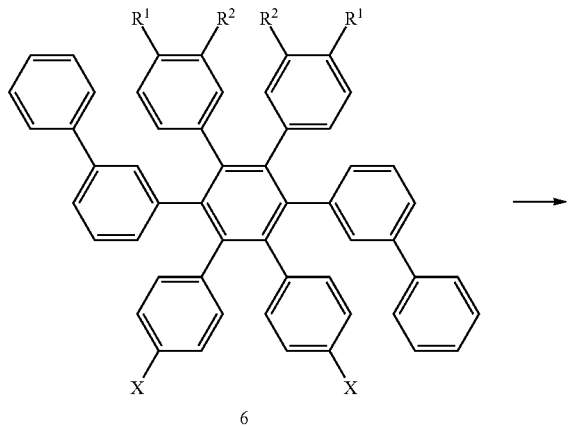

6

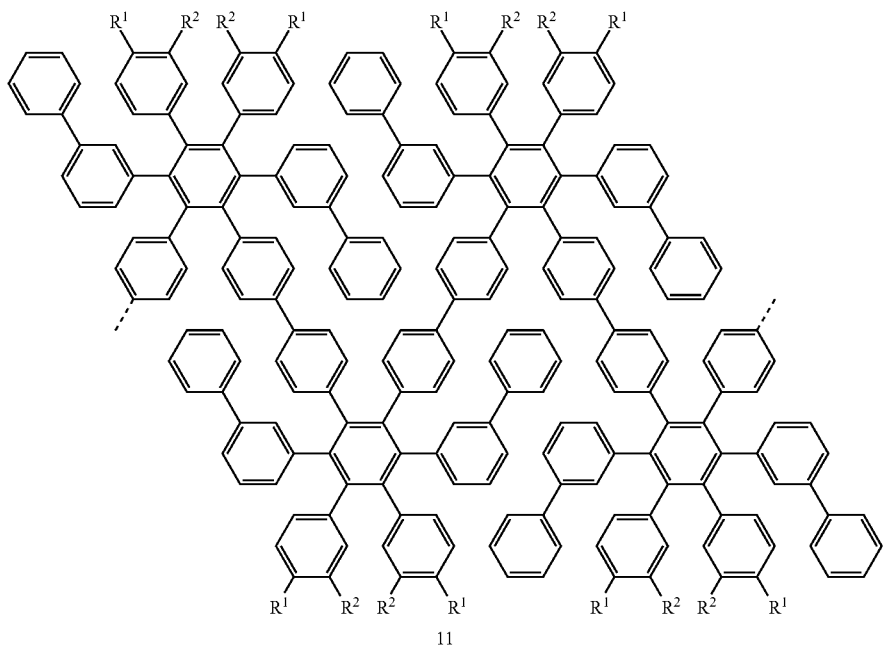

11

The cyclodehydrogenation of the graphene nanoribbon precursors 11 to give the graphene nanoribbons can be effected by means of intramolecular Scholl reaction using, for example, iron(III) chloride as a Lewis acid and oxidizing agent.

In general, the molecular weight of the graphene nanoribbons obtained is 2000 to 100 000, preferably 4000 to 50 000, these molecular weights being determinable by means of GPC.

Graphene nanoribbons can also be produced on metal surfaces. This is done by depositing the monomer on the surface by sublimation. This gives rise to diradicals which are polymerized by a temperature increase to give the graphene nanoribbon precursor. In the last step, further thermal treatment of the substrate results in the cyclodehydrogenation to give the finished graphene nanoribbons (see Cai, J.; et al. Nature 466, 470-473 (2010)).

The invention is illustrated in detail by the examples below.

EXAMPLES

Figure 2:
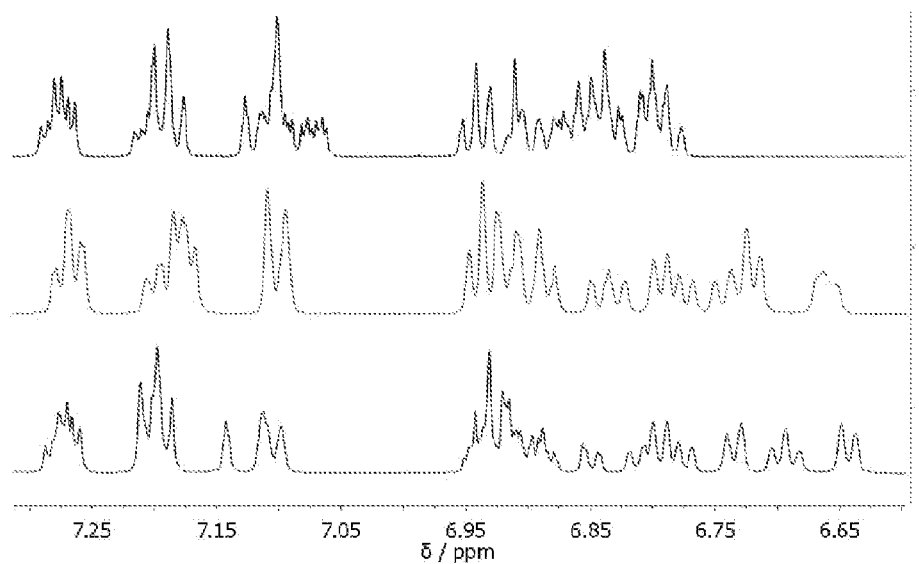
Figure 3:
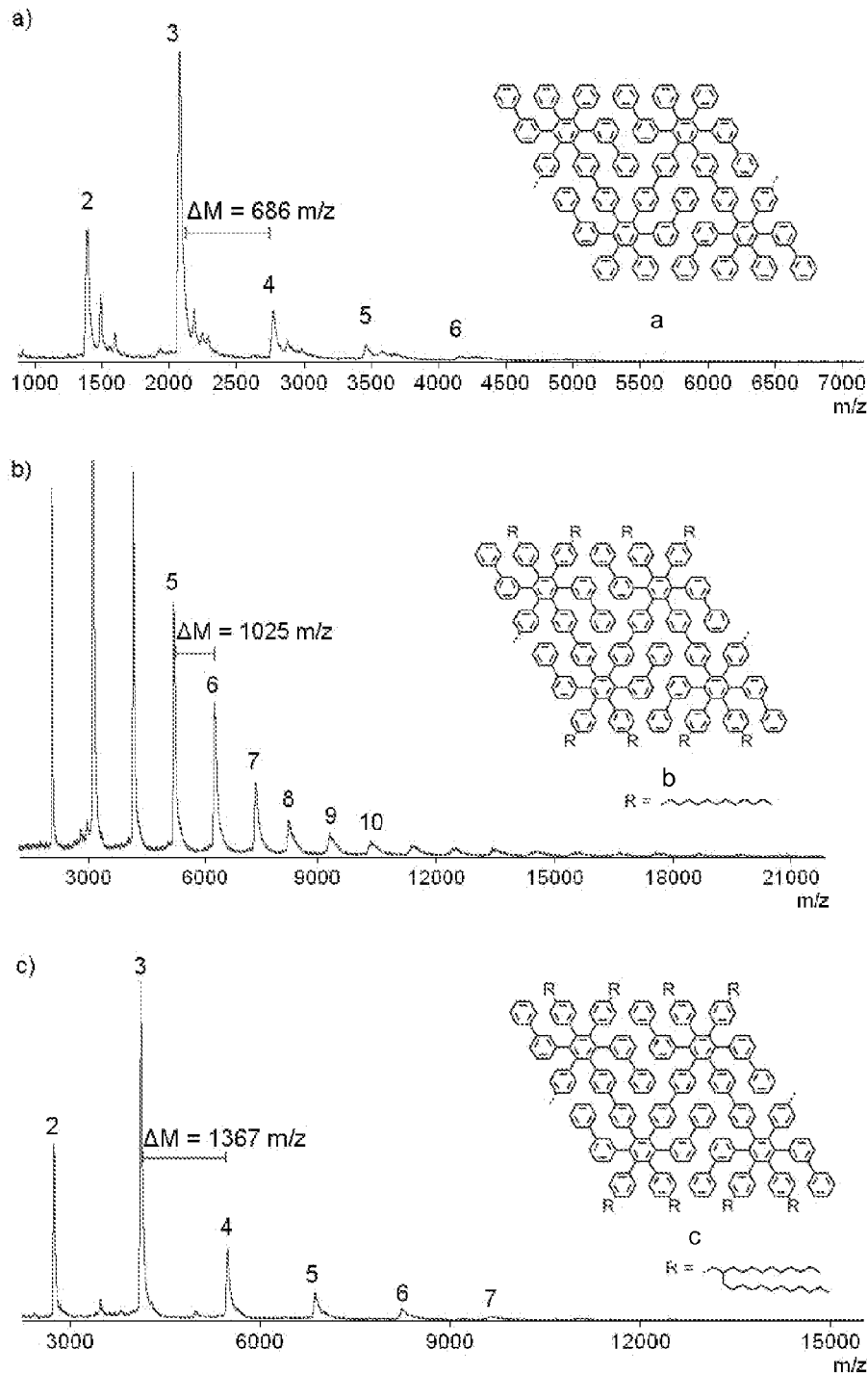
Figure 4:
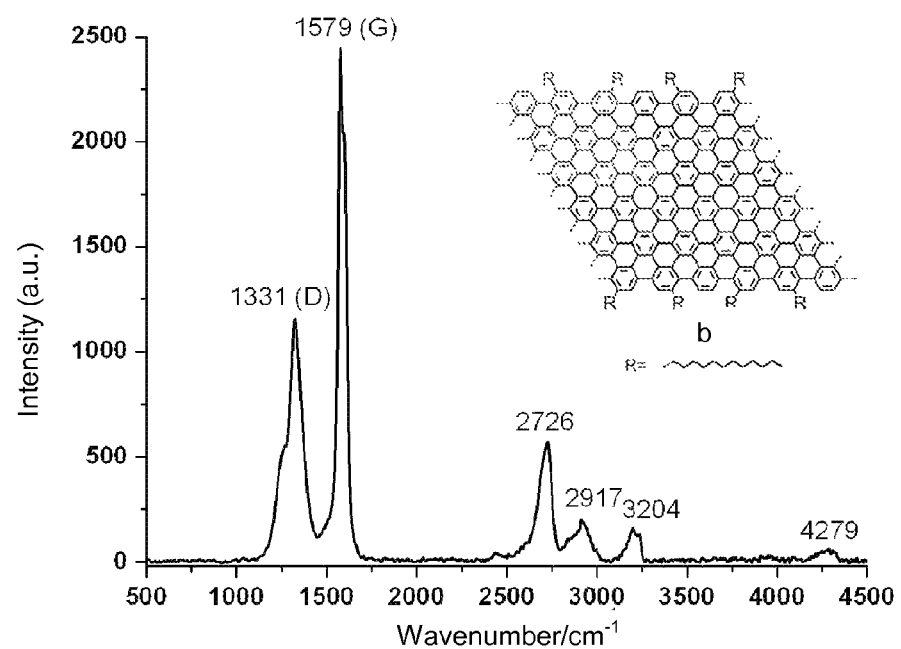
Figure 5:
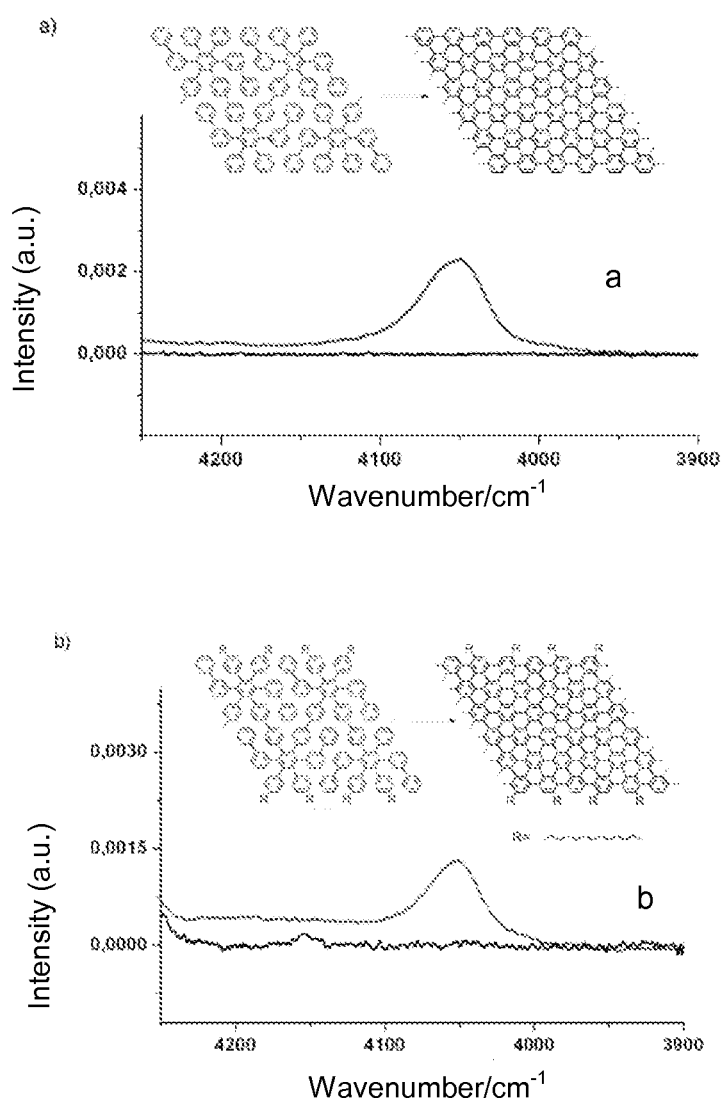

The figures show:
FIG. 1 the superimposed MALDI-TOF mass spectra of the synthesized monomers 6a-c;
FIG. 2 the relevant aromatic region of the $^1$H NMR spectra of the synthesized monomers 6a-c;
FIG. 3 MALDI-TOF mass spectra of the polymer precursors 11a-c;
FIG. 4 the Raman spectrum of the GNR 12b;
FIG. 5 IR spectra of the GNR 12a, b.

Examples 1 to 3

Monomer Synthesis

The synthesis scheme for preparation of monomers of the general formula (II) 6a to 6c is shown in Scheme 5.

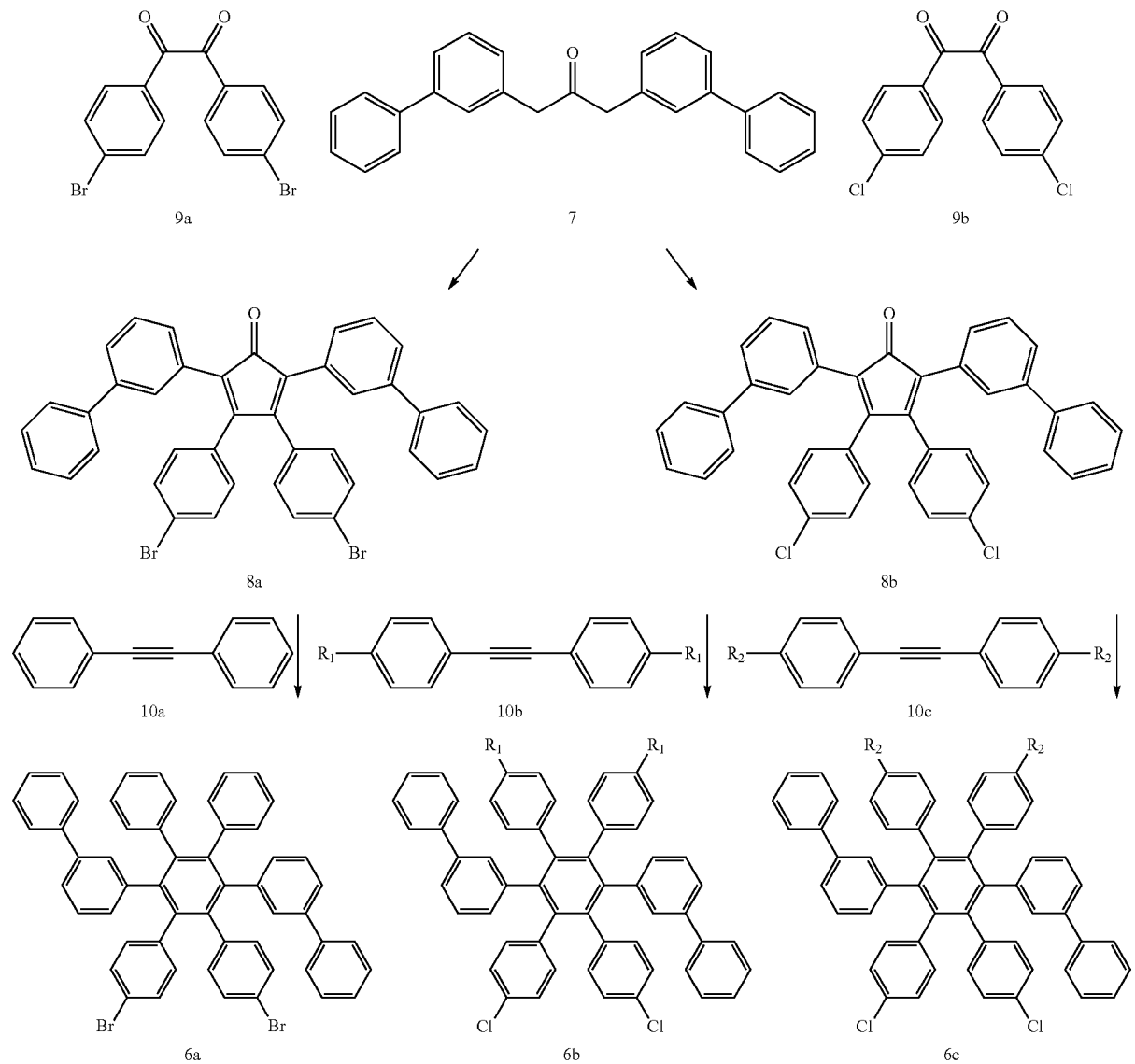

Scheme 5

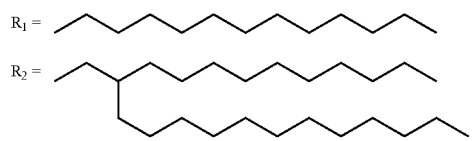

Proceeding from 1,3-di(biphenyl-3-yl)propan-2-one 7, which already comprises the two flexible meta-biphenyl units, Knoevenagel condensation with 4,4'-dibromobenzil 9a or 4,4'-dichlorobenzil 9b using tetrabutylammonium hydroxide as a base introduces two halogen functions for the later Yamamoto polymerization. The tetraarylcyclopentadienones 8a and 8b could not be removed from the reactants by column chromatography, but selected precipitation of the products was possible from DCM in methanol. Thus, 8a was obtained with a yield of 77%, and 8b with 53%, as violet solids. In the last reaction step, the solubility-imparting groups were introduced and the cyclopentadienones were converted by Diels-Alder cycloaddition with functionalized tolanes to give the target compounds. Due to the high steric demands, this reaction had to be performed in a microwave reactor at 220° C. at 300 watts and over a reaction time of 24 h. After column chromatography purification with silica gel and repeated reprecipitation, all monomers were purified by means of recycling GPC. In spite of an associated reduction in yield, this high purity was necessary for the achievement of high molecular weights in the polymerization. Monomer 6a without alkyl radicals was thus obtained in 40% yield as a colorless solid. Addition of 8b with 4,4'-didodecyltolane 10b gave monomer 6b with a yield of 56%, and a reaction with 4,4'-bis(2-decyltetradecyl)tolane 10c gave monomer 6c with 41% yield. Both alkylated products were obtained as colorless oils.

EXAMPLES

Example 1a 2,5-Di([1,1'-biphenyl]-3-yl)-3,4-bis(4-bromophenyl)cyclopenta-2,4-dienone (8a)

To a degassed solution of 2.84 g of 4,4'-dibromobenzil (7.73 mmol) and 2.80 g of 1,3-di(biphenyl-3-yl)propan-2-one (7, 7.73 mmol) in 30 ml of tert-butanol was added, at 80° C., a methanolic tetrabutylammonium hydroxide solution (1 M, 2.84 ml, 2.84 mmol). The reaction solution was stirred at 80° C. for 20 minutes and then stopped by adding water. Extraction was effected three times with dichloromethane, and the collected organic phases were washed with saturated sodium chloride solution and dried over magnesium sulfate before the solvent was distilled off under reduced pressure. The crude product was purified by column chromatography (silica gel, eluent: hexane with 20% DCM) and gave 2.85 g of the tetraarylcyclopentadienone 8a as a violet wax (53%, 4.10 mmol). Elemental analysis measured: C 70.5; H 3.3% (calculated for $C_{41}H_{26}Br_2O$: C, 70.9; H, 3.8%); $^1$H NMR (700 MHz, $d_8$-THF) δ=7.51-7.49 (m, 4H, CH), 7.49-7.46 (m, 4H, CH), 7.41 (dd, J=8.2, 1.1 Hz, 4H, CH), 7.36 (t, J=7.8 Hz, 4H, CH), 7.32 (t, J=8.0 Hz, 2H, CH), 7.29-7.25 (m, 2H, CH), 7.25-7.22 (m, 2H, CH), 7.01-6.99 (m, 4H, CH); $^{13}$C NMR (175 MHz, $d_8$-THF) δ=154.28, 141.92, 141.83, 133.58, 132.72, 132.34, 132.30, 132.12, 129.99, 129.89, 129.71, 129.53, 128.26, 127.80, 127.21, 126.74, 123.92; MS (FD, 8 kV): m/z (%): 693.8 (100) [M$^+$] (calculated for $C_{41}H_{26}Br_2O$: 694.0); Rf (hexane with 6% ethyl acetate)= 0.47.

Example 1b 1,2-Bis(4-bromophenyl)-3,6-bis(biphenyl-3-yl)-4,5-diphenylbenzene (6a)

A degassed solution of 300 mg of 2,5-di([1,1'-biphenyl]-3-yl)-3,4-bis(4-bromophenyl)cyclopenta-2,4-dienone (8a, 0.432 mmol) and 77.0 mg of 4,4'-dibromotolane (0.432 mmol) in 3 ml of diphenyl ether was heated to 230° C. in a microwave reactor at power 300 watts and a maximum pressure of 7 bar for 3×12 h. After cooling to room temperature, the reaction solution was diluted with hexane and purified by column chromatography (silica, hexane with 6% ethyl acetate). After purification by means of recycling GPC and drying under high vacuum, 145 mg of monomer 6a were obtained in the form of colorless crystals (40%, 0.172 mmol). Elemental analysis measured: C 76.7; H 3.1% (calculated for $C_{54}H_{36}Br_2$: C, 76.8; H, 4.3%); $^1$H NMR (700 MHz, $d_8$-THF) δ=7.30-7.25 (m, 4H, CH), 7.23-7.17 (m, 6H, CH), 7.13 (d, J=1.5 Hz, 1H, CH), 7.12-7.11 (m, 1H, CH), 7.11-7.09 (m, 4H, CH), 7.09-7.06 (m, 2H, CH), 6.95 (s, 1H, CH), 6.94 (br s, 2H, CH), 6.93 (s, 1H, CH), 6.91 (t, J=4.1 Hz, 2H, CH), 6.89 (d, J=8.0 Hz, 2H, CH), 6.85 (d, J=7.0 Hz, 4H, CH), 6.83 (d, J=2.0 Hz, 2H, CH), 6.81 (d, J=1.4 Hz, 1H, CH), 6.79 (d, J=8.3 Hz, 2H, CH), 6.78 (s, 1H, CH); $^{13}$C NMR (125 MHz, $d_2$-TCE) δ=141.05, 140.74, 140.20, 140.00, 139.44, 139.03, 138.52, 133.03, 132.92, 131.30, 131.15, 130.26, 129.92, 129.85, 128.42, 127.17, 126.87, 126.62, 126.52, 125.20, 124.15, 120.18, 119.51; MS (MALDI-TOF): m/z (%): 845.1 (100) [M$^+$] (calculated for $C_{54}H_{36}Br_2$: 844.1); Rf (hexane with 6% ethyl acetate)=0.40; m.p. (° C.): decomposition at >400° C.

Example 2a 2,5-Di([1,1'-biphenyl]-3-yl)-3,4-bis(4-chlorophenyl)cyclopenta-2,4-dienone (8b)

To a degassed solution of 940 mg of 4,4'-dichlorobenzil (3.37 mmol) and 1.22 g of 1,3-di(biphenyl-3-yl)propan-2-one (7, 3.37 mmol) in 20 ml of tert-butanol was added, at 80° C., a methanolic tetrabutylammonium hydroxide solution (1M, 1.7 ml, 1.7 mmol). The reaction solution was stirred at 80° C. for 20 minutes, and the reaction then stopped by adding water. The mixture was extracted three times with dichloromethane and the collected organic phases were washed with saturated sodium chloride solution and dried over magnesium sulfate, before the solvent was distilled off under reduced pressure. The crude product was purified by column chromatography (silica gel, eluent: hexane with 20% DCM) and gave 1.56 g of the tetraarylcyclopentadienone 8b as a pale violet solid (77%, 2.58 mmol). Elemental analysis measured: C 81.3; H 3.3% (calculated for $C_{41}H_{26}Cl_2O$: C, 81.3; H, 4.3%); $^1$H NMR (700 MHz, d$_8$-THF) δ=7.52 (s, 2H, CH), 7.50 (d, J=7.8 Hz, 2H, CH), 7.42 (d, J=7.2 Hz, 4H, CH), 7.36 (t, J=7.7 Hz, 4H, CH), 7.32 (m, 6H, CH), 7.27 (t, J=7.3 Hz, 2H, CH), 7.23 (d, J=7.8 Hz, 2H, CH), 7.06 (d, J=8.5 Hz, 4H, CH); $^{13}$C NMR (175 MHz, d$_8$-THF) δ=199.86, 154.28, 141.91, 141.82, 135.61, 133.14, 132.14, 132.10, 129.98, 129.90, 129.70, 129.69, 129.52, 128.27, 127.78, 127.20, 126.73; MS (MALDI-TOF): m/z (%): 604.6 (100) [M$^+$] (calculated for C$_{41}$H$_{26}$Cl$_2$: 604.1); Rf (hexane with 10% ethyl acetate)=0.47.

Example 2b 1,2-Bis(4-chlorophenyl)-3,6-bis(biphenyl-3-yl)-4,5-bis(4-dodecylphenyl)benzene (6b)

A degassed solution of 1.84 g of 2,5-di([1,1'-biphenyl]-3-yl)-3,4-bis(4-chlorophenyl)cyclopenta-2,4-dienone (8b, 3.03 mmol) and 1.72 g of 4,4'-didodecyltolane (3.34 mmol) in 12 ml of diphenyl ether and 5 ml of propylene carbonate was heated to 230° C. in a microwave reactor at power 300 watts and a maximum pressure of 7 bar for 2×12 h. After cooling to room temperature, the reaction solution was diluted with hexane and purified by column chromatography (silica, hexane with 6% ethyl acetate). After purification by means of recycling GPC and drying under high vacuum, 1.85 g of monomer 6b were obtained as a colorless oil (56%, 1.69 mmol). Elemental analysis measured: C 85.6; H 7.9% (calculated for C$_{78}$H$_{84}$Cl$_2$: C, 85.8; H, 7.8%); $^1$H NMR (700 MHz, d$_8$-THF) δ=7.27 (dt, J=7.7, 4.0 Hz, 4H, CH), 7.22-7.16 (m, 6H, CH), 7.10 (d, J=10.0 Hz, 4H, CH), 6.94 (t, J=7.7 Hz, 4H, CH), 6.91 (s, 2 Hv), 6.88 (d, J=8.4 Hz, 2H, CH), 6.87-6.81 (m, 2H, CH), 6.81-6.77 (m, 2H, CH), 6.77-6.70 (br m, 6H, CH), 6.66 (d, J=7.5 Hz, 2H, CH), 2.41-2.28 (m, 4H, α-CH$_2$), 1.44-1.34 (m, 4H, β-CH$_2$), 1.34-1.03 (m, 36H, —CH$_2$—), 0.89 (t, J=6.9 Hz, 6H, —CH$_3$); $^{13}$C NMR (175 MHz, d$_8$-THF) δ=142.44, 142.42, 142.27, 141.88, 141.74, 140.76, 140.74, 140.68, 140.59, 140.56, 140.14, 140.10, 139.09, 139.05, 134.18, 134.14, 134.06, 134.01, 132.56, 132.50, 132.47, 132.30, 132.26, 131.69, 131.41, 129.37, 128.20, 128.07, 127.90, 127.88, 127.84, 127.81, 127.80, 127.74, 125.14, 125.12, 36.36, 36.33, 33.06, 32.37, 32.34, 30.85, 30.81, 30.77, 30.75, 30.61, 30.60, 30.51, 30.00, 29.98, 25.94, 25.82, 23.74, 14.62; MS (MALDI-TOF): m/z (%): 1091.0 (100) [M$^+$] (calculated for C$_{78}$H$_{84}$Cl$_2$: 1090.6); Rf (hexane with 6% ethyl acetate)=0.65.

Example 3

1,2-Bis(4-chlorophenyl)-3,6-bis(biphenyl-3-yl)-4,5-bis(4-(2-decyltetradecyl)dodecylphenyl)benzene (6c)

A degassed solution of 636 mg of 2,5-di([1,1'-biphenyl]-3-yl)-3,4-bis(4-chlorophenyl)cyclopenta-2,4-dienone (8b, 1.05 mmol) and 895 mg of 4,4'-bis(2-decyltetradecyl)tolane (1.05 mmol) in 10 ml of diphenyl ether was heated to 230° C. in a microwave reactor at power 300 watts and a maximum pressure of 7 bar for 2×12 h. After cooling to room temperature, the reaction solution was diluted with hexane and purified by column chromatography (silica, hexane with 6% ethyl acetate). After purification by means of recycling GPC and drying under high vacuum, 613 mg of monomer 6c were obtained as a colorless oil (41%, 0.429 mmol). Elemental analysis measured: C 86.0; H 9.7% (calculated for C$_{102}$H$_{132}$Cl$_2$: C, 85.8; H, 9.3%); $^1$H NMR (700 MHz, d$_8$-THF) δ=7.29-7.25 (m, 4H, CH), 7.20 (m, 6H, CH), 7.14 (s, 1H, CH), 7.11 (d, J=10.0 Hz, 3H, CH), 6.95-6.88 (m, 9H, CH), 6.85 (d, J=8.4 Hz, 1H, CH), 6.81 (d, J=8.0 Hz, 1H, CH), 6.79 (d, J=7.8 Hz, 2H, CH), 6.77 (d, J=7.7 Hz, 1H, CH), 6.73 (d, J=7.8 Hz, 2H, CH), 6.69 (t, J=7.6 Hz, 2H, CH), 6.64 (d, J=7.9 Hz, 2H, CH), 2.33-2.24 (m, 4H, α-CH$_2$), 1.44-1.37 (m, 2H, β-CH$_2$), 1.35-0.95 (br m, 80H, —CH$_2$—), 0.89 (m, 12H, —CH$_3$); $^{13}$C NMR (175 MHz, d$_8$-THF) δ=142.43, 142.41, 142.20, 142.18, 141.94, 141.77, 140.69, 140.65, 140.55, 140.52, 140.10, 140.07, 139.61, 139.08, 134.13, 134.04, 133.98, 132.48, 132.31, 132.13, 131.70, 131.37, 129.41, 128.67, 128.53, 128.21, 128.07, 127.87, 127.77, 125.08, 40.92, 40.61, 33.94, 33.86, 33.81, 33.08, 33.06, 31.20, 31.12, 31.10, 30.89, 30.86, 30.82, 30.54, 30.52, 27.49, 27.45, 25.93, 25.82, 23.76, 23.75, 14.63; MS (MALDI-TOF): m/z (%): 1427.8 (100) [M$^+$] (calculated for C$_{102}$H$_{132}$Cl$_2$: 1428.0); Rf (hexane with 6% ethyl acetate)= 0.76.

FIG. 1 shows the superimposed MALDI-TOF mass spectra of the synthesized monomers 6a-c. It was possible in all three cases to obtain the products in pure form and to ensure that no by-products which could have caused termination of chain growth during the later polymerization were present any longer. The exact structure of the monomers was confirmed by $^1$H NMR spectroscopy.

FIG. 2 shows the relevant aromatic region of the $^1$H NMR spectra of monomers 6a-c, recorded in d$_8$-THF (700 MHz, RT). The $^1$H NMR spectra of monomers 6a-c can be resolved only with difficulty since all 34 to 36 aromatic protons exhibited a very similar chemical shift. The signals are within a narrow range from 6.6 to 7.3 ppm, and some are superimposed. By means of DOSY (diffusion-ordered spectroscopy), the diffusion properties of the molecules in the sample can be determined, and COSY experiments can determine couplings between the signals of conjugated protons in the NMR.

Examples 4 to 6

Polymer Synthesis

Once the structure and purity of monomers 6a-c had been confirmed, the corresponding polymers were synthesized by Yamamoto polymerization according to Scheme 6.

Scheme 6
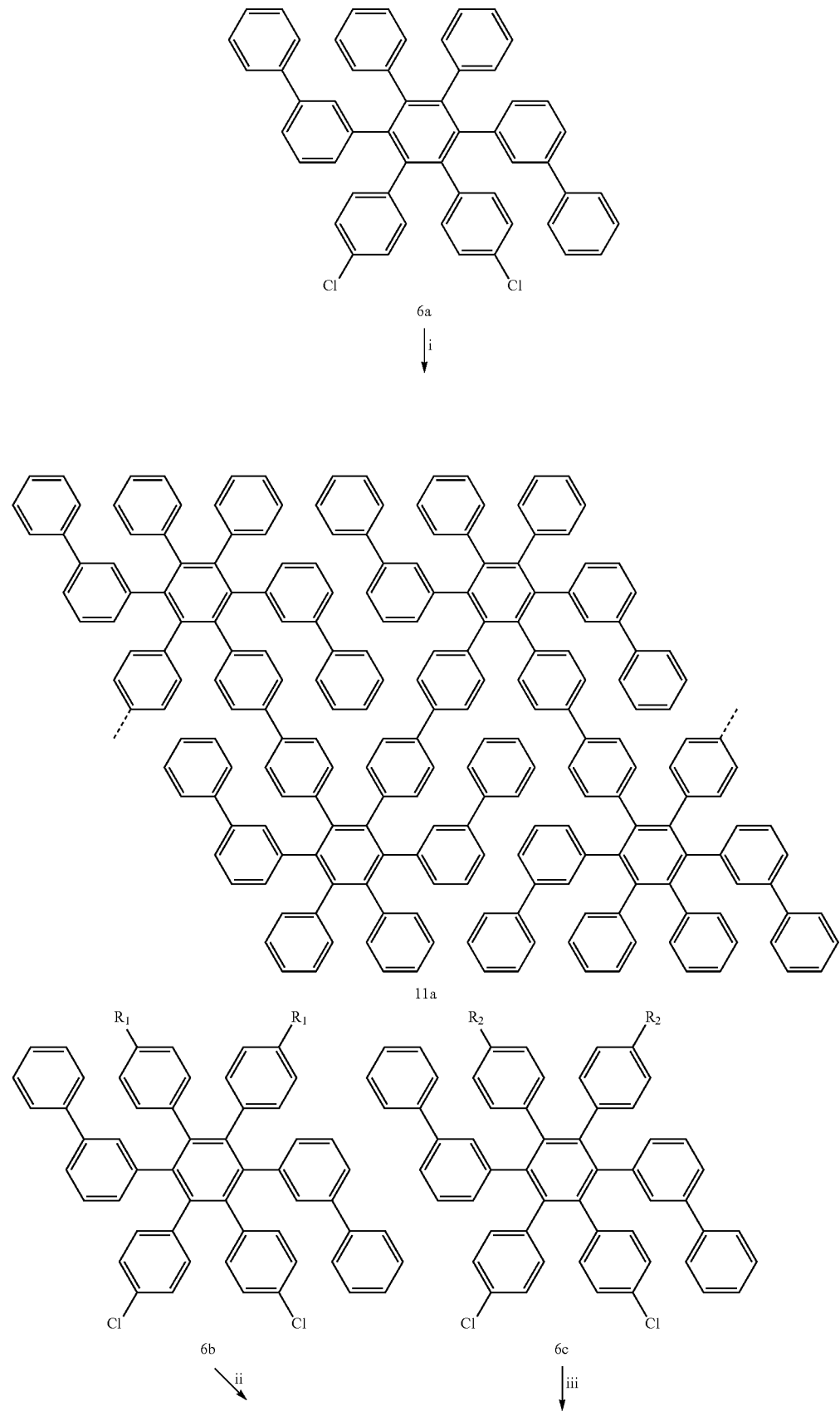

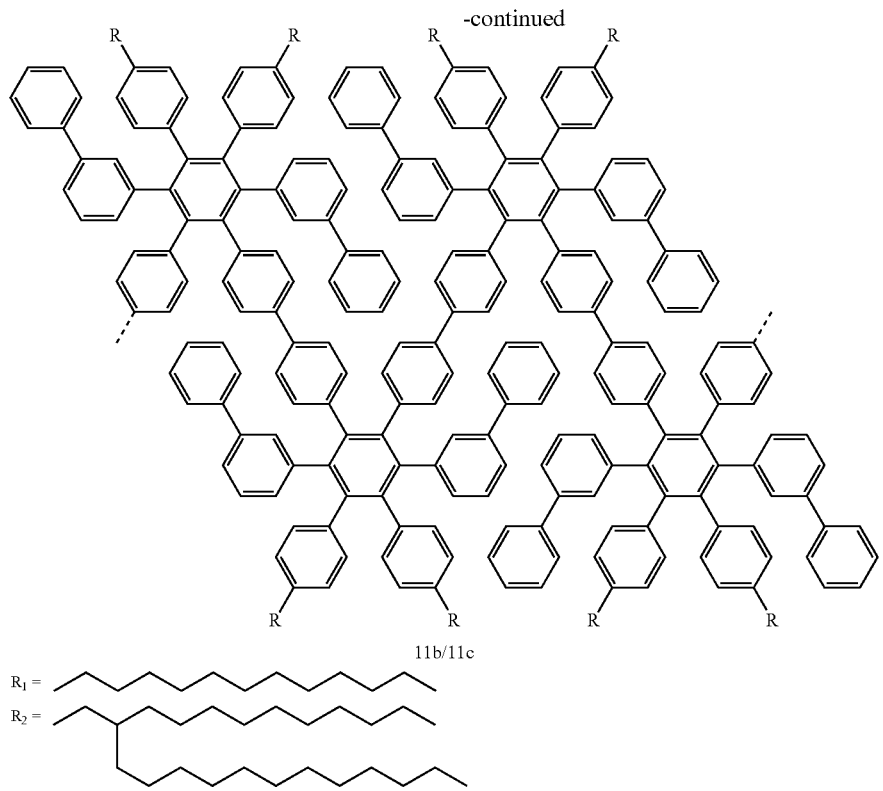

11b/11c $R_1 =$ [structure]

$R_2 =$ [structure]

Scheme 6 shows the synthesis of the graphene nanoribbon precursors 11a-c by Yamamoto polymerization of the dihalogenated monomers 6a-c with catalysis by Ni(COD)$_2$, 1,5-cyclooctadiene and 2,2'-bipyridine in toluene/DMF. The yields were (i) 84%, (ii) 86%, (iii) 67%. Since the catalytically active nickel(0) reagent in the Yamamoto polycondensation is very sensitive to water and oxygen, all monomer units 6 were dried under high vacuum before they were used for the polymerization. The catalyst mixture composed of 59.4 mg of Ni(COD)$_2$, 23.4 mg of 1,5-cyclooctadiene and 33.7 mg of 2,2'-bipyridine (0.216 mmol of each) was weighed out in a glovebox under an argon atmosphere and prepared together with the solvents in a microwave-compatible glass reaction vessel, sealed with a gas-tight aluminum lid with septum and protected from any incident light. The use of a microwave reactor to conduct the reaction gives the advantage of a distinctly increased reaction rate and a reaction temperature above the boiling point of the solvents. After the thermal activation of the catalyst at 60° C. for 20 minutes, a degassed solution of 0.09 mmol of the monomer in 1 ml of anhydrous toluene was introduced into the reaction vessel through the septum, and the polymerization was performed at microwave power 300 watts and 80° C. over a period of 10 hours. A monomer concentration of about 50 mg/ml was used to promote the attainment of high molecular weights. To end-cap the polymers, a degassed solution of bromo-/chlorobenzene in toluene (0.5 ml, 0.01 molar) was finally added, and the mixture was heated again to 80° C. for 20 minutes. To purify the products and remove catalyst residues, the reaction solution was added dropwise to an HCl/methanol mixture and stirred overnight. The resulting precipitate was removed in a centrifuge and repeatedly reprecipitated with THF in methanol, before it was filtered off and dried under reduced pressure. The polymers 11a without alkyl radicals and 11b with dodecyl chains were obtained in yields of 84 to 86% as colorless solids. Only by the introduction of branched 2-decyltetradecyl radicals was the melting point lowered to such an extent that the polymer 11c was present as a colorless oil at room temperature. Before the subsequent cyclodehydrogenation to give the corresponding GNRs, low molecular weight oligomers were removed by a manual preparative GPC fractionation. This was possible since all three polymers were fully soluble in common organic solvents such as THF, DCM or toluene.

Example 4

The monomer used was 76.0 mg of 1,2-bis(4-bromophenyl)-3,6-bis(biphenyl-3-yl)-4,5-diphenylbenzene (6a, 0.09 mmol). After conclusion of the reaction and cooling to room temperature, a colorless precipitate had already formed. After purification of the crude product, 43.7 mg of the polymer 11a were obtained as a colorless solid (84%). GPC analysis: Mn=0.11×10$^4$ g/mol, M$_w$=0.15×10$^4$ g/mol, polydispersity D=1.35 (UV detector, PS standard), DSC (° C.): no transitions.

Example 5

The monomer used was 98.3 mg of 1,2-bis(4-bromophenyl)-3,6-bis(biphenyl-3-yl)-4,5-bis(4-dodecylphenyl)benzene (6b, 0.09 mmol). After conclusion of the reaction and cooling to room temperature, the reaction solution had turned dark brown, and there was a black precipitate on the flask wall. After purification of the crude product, 79.0 mg of polymer 11b were obtained as a colorless solid (86%). GPC analysis: M$_n$=0.93×10$^4$ g/mol, M$_w$=1.25×10$^4$ g/mol, polydispersity D=1.34 (UV detector, PS standard), DSC (° C.): no transitions.

Example 6

The monomer used was 128.6 mg of 1,2-bis(4-bromophenyl)-3,6-bis(biphenyl-3-yl)-4,5-bis(4-(2-decyltetradecyl)dodecylphenyl)benzene (6c, 0.09 mmol). After conclusion of the reaction and cooling to room temperature, the reaction solution had turned dark brown, and there was a black precipitate on the flask wall. After purification of the crude product, 81.9 mg of polymer 11c were obtained as a colorless oil (67%). GPC analysis: $M_n=0.35\times10^4$ g/mol, $M_w=0.48\times10^4$ g/mol, polydispersity D=1.37 (UV detector, PS standard), DSC (° C.): no transitions.

The molecular weights attained in polymers 11a-c were determined by MALDI-TOF MS and GPC analysis. Since no suitable standard was available for a GPC analysis, a polystyrene standard was used due to the angled backbone of the polymers. MALDI-TOF MS is subject to the limitation that detection of high molecular weight species was impossible due to the polydispersity of the samples. The data obtained here therefore permit only conclusions about the minimum molecular weights in the sample. The MALDI-TOF mass spectra recorded for polymer precursors 11a-c are reproduced in FIG. 3.

The analysis of polymers 11a-c by means of MALDI-TOF MS showed that very regular signal patterns were observed in all cases, for which there was a high level of correspondence between the spacings of the signals and the calculated molecular weights of the respective repeat units. In the case of 11a, the intense signals were assigned to the fully debrominated product. The weak signals arose through adsorption of silver ions during the ionization, and were not observed in reflector mode. It was possible to detect molecular weights up to 5000 g/mol, which corresponded to a maximum of seven repeat units. In the case of polymer 11b with dodecyl chains, molecular weights of up to 20 000 g/mol (19 repeat units) were detected. In the case of polymer 11c, seven repeat units with a molar mass up to 10 000 g/mol were detected.

Since all three polymers 11a-c (apart from the alkyl radicals) had the same repeat unit, it was easily possible to convert the molecular weights to the chain length. This length corresponded to the later longitudinal dimension of the GNRs after the cyclodehydrogenation. For the graphene nanoribbon precursor 11b with dodecyl chains, the molar mass of 20 000 g/mol corresponded to a later graphene ribbon with a width of 2.1 nm and a length of about 12 nm (~1.2 nm/repeat unit).

Examples 7 to 9

Cyclodehydrogenation

The cyclodehydrogenation of the polymer precursors 11a-c to give the corresponding GNRs 12a-c according to Scheme 7 was performed by means of intramolecular Scholl reaction using iron(III) chloride as the Lewis acid and oxidizing agent.

Scheme 7

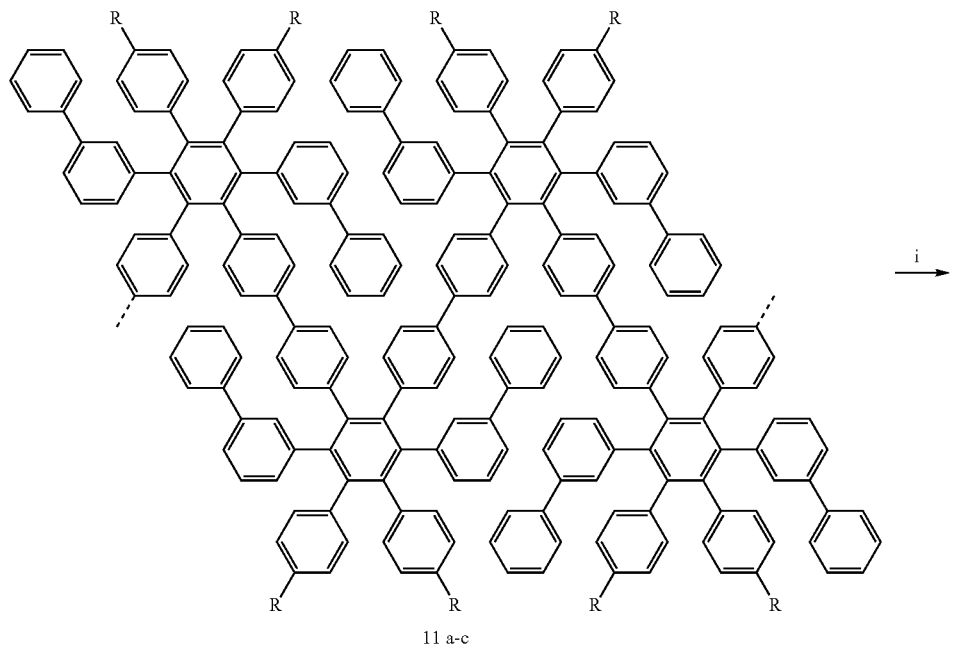

11 a-c

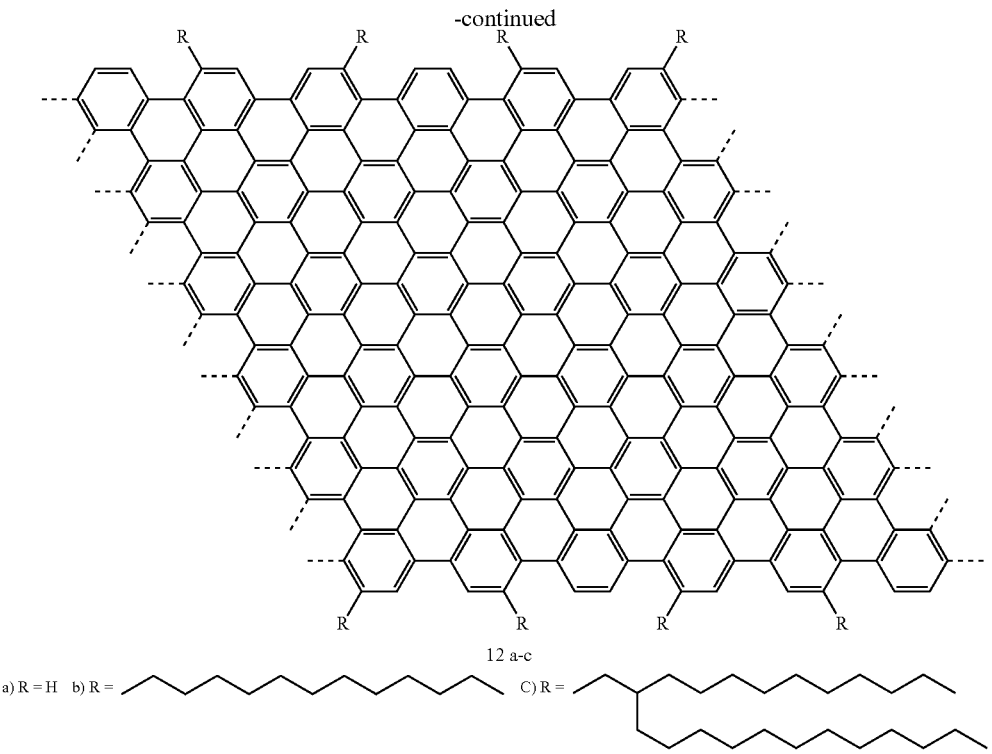

12 a-c a) R = H    b) R = ~~~~~~~~~    C) R = ~~~~~~~~~

Typically, the reaction was performed with a very low polymer concentration of 1 mg/ml in unstabilized dichloromethane in order to prevent the occurrence of intermolecular aryl-aryl couplings. The reaction solutions were degassed with an argon stream over the entire reaction time in order to drive out oxygen and the HCl which formed. At the start of the reaction, six equivalents of iron(III) chloride per bond to be formed (90 equivalents per repeat unit) were added rapidly as a concentrated solution in nitromethane, and the mixture was stirred at room temperature for three days. After the cyclodehydrogenation had concluded, the GNRs were precipitated with methanol and purified further.

GNR 12a without alkyl radicals and GNR 12b with dodecyl radicals were obtained with a yield of 64 and 98% as black solids, which were insoluble in standard organic solvents such as toluene, THF, tetrachloroethane or chloroform. With a width of the graphene ribbon of 2.1 nm, there were such strong π-π interactions that two dodecyl radicals per repeat unit in the case of 12b were insufficient to prevent aggregation. For workup, the crude products were therefore freed of all soluble impurities by Soxhlet extraction with THF and methanol, and finally dried under high vacuum. GNR 12c with 2-decyltetradecyl chains, in contrast, was obtained in a yield of 81% as a black solid, which was soluble in standard organic solvents such as THF or toluene. The purification was therefore effected by repeated reprecipitation from THF in methanol and subsequent Soxhlet extraction with acetone, in order to remove impurities, by-products products and inorganic residues.

Example 7

50 mg of polymer precursor 11a were reacted with 1.12 g of FeCl$_3$ (6.87 mmol, dissolved in 4 ml of nitromethane). After a reaction time of three days, a black precipitate had already formed, which was removed in a centrifuge. For purification, the crude product was in each case subjected to a two-day Soxhlet extraction with THF and methanol, and finally dried under high vacuum. Thus, 32.0 mg of the GNR 12a were obtained as a black insoluble solid (64%). DSC (° C.): no transitions.

Example 8

76.6 mg of polymer precursor 11b were reacted with 1.10 g of FeCl$_3$ (6.76 mmol, dissolved in 3.5 ml of nitromethane). After a reaction time of three days, a black precipitate had already formed, which was removed in a centrifuge. For purification, the crude product was in each case subjected to a two-day Soxhlet extraction with THF and methanol, and finally dried under high vacuum. Thus, 72.9 mg of the GNR 12b were obtained as a black insoluble solid (98%). DSC (° C.): no transitions.

Example 9

38.11 mg of polymer precursor 11c were reacted with 410 mg of FeCl$_3$ (2.53 mmol, dissolved in 1.3 ml of nitromethane). After addition of the methanol, a black precipitate formed, which was removed in a centrifuge and freed of all impurities, by-products and inorganic residues by reprecipitation from THF in methanol and subsequent two-day Soxhlet extraction with acetone. After drying under high vacuum, 30.2 mg of the GNR 12c were obtained as a black solid (81%). DSC (° C.): no transitions.

The complete cyclodehydrogenation and the defect-free structure of the GNRs 12a-c were demonstrated by means of Raman and IR spectroscopy. FIG. 4 shows the Raman spectrum of the GNR 12b, recorded in a thin powder film with laser excitation at λ=488 nm. Raman spectroscopy allowed relevant information about the extent of the π-system within the GNRs to be obtained, and thus the conjugation length to be calculated. By IR absorption measurements, it was possible to examine the presence of a band at 4050 cm$^{-1}$ for all samples, which was characteristic of the free rotation of phenyl rings and, in the case of full cyclodehydrogenation, was no longer detectable.

GNR 12b was the only sample which showed no fluorescence in the solid state, and thus allowed the recording of Raman spectra on thin powder films with a laser excitation wavelength of 488 nm. The spectrum obtained is shown in FIG. 4. Good resolution was obtained both for the characteristic D band at 1331 cm$^{-1}$ and the sharp G band at 1579 cm$^{-1}$. The position of these bands corresponded to a high degree with values known from literature for graphene ribbons, which confirmed the graphene character of the sample. At multiples of these wavenumbers, it was also possible to find the second- and third-order signals. For a calculation of the dimensions $L_a$ of the GNR 12b, the ratio of the integrals (I) of first-order D and G bands was converted by the formula $I(D)/I(G)=C(\lambda)/L_a$. $C(\lambda)$ was a wavelength-dependent factor, which assumed the value $C(\lambda)=4.4$ nm for $\lambda=488$ nm. Thus, a dimension of 4.6 to 4.7 nm was calculated, which corresponded to a graphene ribbon with about eight repeat units and a molecular weight of about 8000 g/mol.

The completeness of the cyclodehydrogenation of the GNRs 12a and 12b was additionally confirmed by IR spectroscopy. FIG. 5 shows the IR spectra of the GNRs 12a and 12b. The band at 4050 cm$^{-1}$ was characteristic in each case of the free rotation of phenyl rings, and it was observed clearly in the spectrum of the polymer precursors 11a and 11b (upper lines). After conclusion of the cyclodehydrogenation, complete absence of this band (lower lines) ruled out the presence of uncondensed phenyl rings in the molecules, and hence proved the complete cyclodehydrogenation.

The invention claimed is:

1. A graphene nanoribbon precursor comprising repeat units of general formula (I)

(I)

in which $R^1$, $R^2$ are each H, halogen, —OH, —NH$_2$, —CN, —NO$_2$ or a hydrocarbyl radical which has 1 to 40 carbon atoms and may be linear or branched, saturated or unsaturated and mono- or polysubstituted by halogen (F, Cl, Br, I), —OH, —NH$_2$, —CN and/or —NO$_2$, where one or more CH$_2$ groups may also be replaced by —O—, —S—, —C(O)O—, —O—C(O)—, —C(O)—, —NH— or —NR—, in which R is an optionally substituted C$_1$-C$_{40}$-hydrocarbyl radical, or an optionally substituted aryl, alkylaryl or alkoxyaryl radical.

2. A process for preparing graphene nanoribbon precursors, comprising the Yamamoto coupling reaction of monomers of the general formula (II)

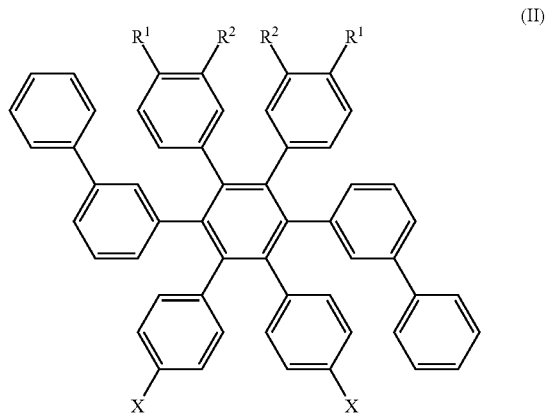

(II)

in which $R^1$, $R^2$ are each H, halogen, —OH, —NH$_2$, —CN, —NO$_2$ or a hydrocarbyl radical which has 1 to 40 carbon atoms and may be linear or branched, saturated or unsaturated and mono- or polysubstituted by halogen (F, Cl, Br, I), —OH, —NH$_2$, —CN and/or —NO$_2$, where one or more CH$_2$ groups may also be replaced by —O—, —S—, —C(O)O—, —O—C(O)—, —C(O)—, —NH— or —NR—, in which R is an optionally substituted C$_1$-C$_{40}$-hydrocarbyl radical, or an optionally substituted aryl, alkylaryl or alkoxyaryl radical, and X is halogen, trifluoromethylsulfonate or diazonium.

3. A process for preparing monomers of the gene a formula (II), comprising the steps of (i) reacting 1,3-di(biphenyl-3-yl)propan-7-one 7

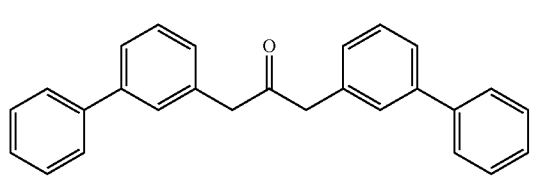

7 with 4,4'-dihalobenzil 9

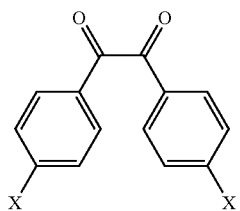

by Knoevenagel condensation to give the tetraarylcyclopentadienone 8

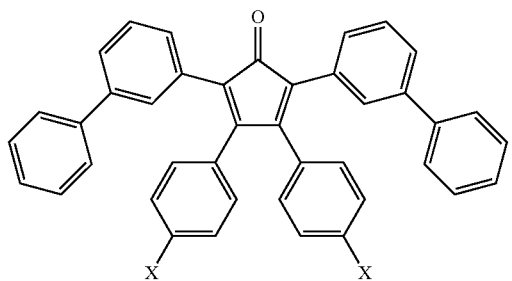

(ii) reacting the tetraarylcyclopentadienone 8 with a tolane 10

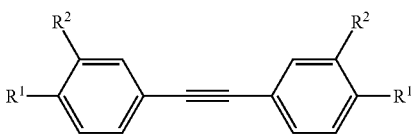

by Diels-Alder reaction to give the monomer of the general formula (II)

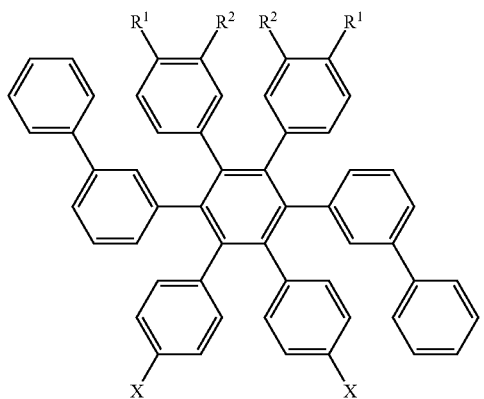

in which $R^2$ are each H, halogen, —OH, —NH$_2$, —CN, —NO$_2$ or a hydrocarbyl radical which has 1 to 40 carbon atoms and may be linear or branched, saturated or unsaturated and mono- or polysubstituted by halogen (F, Cl, Br, I), —OH, —NH$_2$, —CN and/or —NO$_2$, where one or more CH$_2$ groups may also be replaced by —O—, —S—, —C(O)O—, —O—C(O)—, —C(O)—, —NH— or —NR—, in which R is an optionally substituted $C_1$-$C_{40}$-hydrocarbyl radical, or an optionally substituted aryl, alkylaryl or alkoxyaryl radical, and X is halogen, trifluoromethylsulfonate or diazonium.

4. A monomer for preparation of graphene nanoribbon precursors by Yamamoto coupling reaction, of the general formula (II)

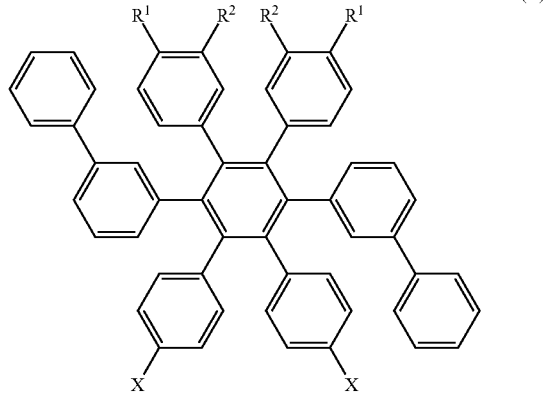

in which $R^1$, $R^2$ are each H, halogen, —OH, —NH$_2$, —CN, —NO$_2$ or a hydrocarbyl radical which has 1 to 40 carbon atoms and may be linear or branched, saturated or unsaturated and mono- or polysubstituted by halogen (F, Cl, Br, I), —OH, —NH$_2$, —CN and/or where one or more CH$_2$ groups may also be replaced by —O—, —C(O)O—, —O—C(O)—, —C(O)—, —NH— or —NR—, in which R is an optionally substituted $C_1$-$C_{40}$-hydrocarbyl radical, or an optionally substituted aryl, alkylaryl or alkoxyaryl radical, and X is halogen, trifluoromethylsulfonate or diazonium.

* * * * *